United States Patent [19]

Ichikawa et al.

[11] Patent Number: 5,798,274
[45] Date of Patent: *Aug. 25, 1998

[54] METHOD FOR SELECTING MONOCLONAL ANTIBODIES FOR HUMAN G-CSF PERMITTING LOW-LEVEL DETECTION IN HUMAN FLUIDS

[75] Inventors: Takanori Ichikawa, Takasaki; Tomoaki Kuwaki, Maebashi; Shigeru Matsuki, Takasaki; Katsumi Tachibana, Maebashi, all of Japan

[73] Assignee: Kirin-Amgen, Inc., Wilmington, Del.

[*] Notice: The portion of the term of this patent subsequent to Feb. 22, 2014, has been disclaimed.

[21] Appl. No.: 477,328

[22] Filed: Jun. 7, 1995

Related U.S. Application Data

[62] Division of Ser. No. 199,493, Feb. 22, 1994, Pat. No. 5,468,846.

[30] Foreign Application Priority Data

Jun. 30, 1993 [JP] Japan ................................. 5-162268

[51] Int. Cl.$^6$ .................... G01N 33/531; G01N 33/543
[52] U.S. Cl. .................... 436/518; 435/7.92; 435/7.93; 435/7.94; 435/7.95; 435/70.21; 436/548; 530/388.23
[58] Field of Search .................... 435/7.92, 7.93, 435/7.94, 7.95, 70.21, 240.27; 436/518, 548; 530/388.23

[56] References Cited

U.S. PATENT DOCUMENTS

| 5,164,299 | 11/1992 | Lambert | 435/7.92 |
| 5,468,846 | 11/1995 | Ichikawa et al. | 530/388.23 |

FOREIGN PATENT DOCUMENTS

| A-225583 | 6/1987 | European Pat. Off. . |
| A-5115297 | 2/1976 | Japan . |
| A-2287257 | 11/1990 | Japan . |
| WO87/03689 | 6/1987 | WIPO . |

OTHER PUBLICATIONS

Goding, James W., "Monoclonal Antibodies: Principles and Practice", 1983, pp. 72–84.

Hellström, K.E. et al., in Monoclonal Antibodies for Cancer Detection and Therapy, Baldwin et al., eds., Orlando, FL: Academic Press, 1985.

Kiriyama, R. et al., *Japanese Journal of Clinical Hematology*, 33(10):1544 (1992).

Kurotani, W. et al., *Japanese Journal of Clinical Hematology*, 34(10):1307 (1993).

Motojima, H. et al., "Quantitative enzyme immunoassay for human granulocyte colony stimulation factor (G-CSF)," *Journal of Immunological Methods*, 118:187–192 (1989).

Omori, F. et al., "Measurement of Human G-CSF by Enzyme–linked Immunoabsorbent Assay Using Monoclonal Antibody," *Research in Experimental Medicine*, 189:163–171 (1989).

Omori, F. et al. "Levels of human serum granulocyte colony-stimulating factor and granulocyte–macrophage colony-stuimulating factor under pathological conditions," *Biotherapy*, 4:147–153 (1992).

Sevier, E.D. et al., "Monoclonal Antibodies in Clinical Immunology," *Clinical Chemistry*, 27(11):1797–1806 (1981).

Shimamura, K. et al., "Establishment of Specific Monoclonal Antibodies Against Recombinant Human Granulocyte Colony Stimulating factor . . . ." *Journal of Histochemistry & Cytochemistry*, 36(2):283–286 (1990).

Tachibana, K. et al., *International Journal of Hematology*, 55(1):202 (1992).

Watari, K. et al., "Serum Granulocyte Colony–Stimulating Factor Levels in Healthy Volunteers and Patients with Various Disorders as Estimated by Enzyme Immunoassay," *Blood*, 73:117–122 (1989).

*Primary Examiner*—Christopher L. Chin
*Attorney, Agent, or Firm*—Marshall, O'Toole, Gerstein, Murray & Borun

[57] ABSTRACT

The present invention relates to a high affinity monoclonal antibody for human G-CSF and to an enzyme immunoassay using said antibody. Specifically, the practice of the invention permits one skilled in the art to obtain monoclonal antibodies with the characteristics necessary to permit low-level detection of G-CSF in plasma of equal to or less than 0.5 pg/ml in an immunoassay without interference in human fluids.

5 Claims, 3 Drawing Sheets

METHOD FOR SELECTING MONOCLONAL ANTIBODIES FOR HUMAN G-CSF PERMITTING LOW-LEVEL DETECTION IN HUMAN FLUIDS

This is a divisional of U.S. application Ser. No. 08/199,493 filed Feb. 22, 1994, which issued as U.S. Pat. No. 5,468,846 on Mar. 21, 1995.

BACKGROUND OF THE INVENTION

1. Field of the Invention

This invention relates to an enzyme immunoassay highly sensitive to a trace amount of human G-CSF, especially, in body fluids.

2. Description of Related Art

G-CSF is a hematopoietic factor which has been found in the culture of a human bladder cancer cell line 5637 (ATCC HT8-9) (Welt et al., *Proc. Natl. Acad. Sci. U.S.A.*, 82, 1526–1530 (1985)). The DNA sequence of its gene has been determined (JP-A-63-50636), which has made it possible to produce the G-CSF by the recombinant DNA techniques.

It has been reported that G-CSF is a factor which acts on myeloid stem cells and enhances their differentiation into neutrophilic leukocytes (Metcalf et al., *Blood*, 67 (1), 37–45 (1986)), and that it also stimulates functions of differentiated neutrophilic leukocytes such as phagocytosis, $O_2^-$-production and the like (Yuo et al., *Blood*, 70 (2), 404–411 (1987)). Also, the G-CSF can effectively enhance the restoration of neutrophilic leukocytes when administered to patients with the clinical condition such as neutropenia which is caused by administration of chemotherapeutic drugs. When the G-CSF is applied clinically, it is necessary to clarify the correlation between a therapeutic effect and a G-CSF level in biological fluids. For the purpose, the level of G-CSF in the biological fluids must be determined accurately.

In addition, it has been reported that the G-CSF exists at either higher or lower concentrations in the sera of patients with hematological disorders in comparison with those of healthy persons (Watari et al., *Blood*, 73, 117–122 (1989); Ohmori et al., *Biotherapy*, 4, 147–153 (1992); *International Journal of Hematology*, vol.57, Supplement No.1, p.235). The highly sensitive measurement of G-CSF will therefore become an effective means, for instance, in the investigations on the relationship between the G-CSF level in the body and the etiology associated with G-CSF.

Interference is a general problem in the measurement of components in the body fluid such as plasma. This is a phenomenon that a body fluid component makes interference with an antigen-antibody reaction in a non-specific or specific fashion to generally cause the inhibition of the reaction, resulting in a serious decrease in a sensitivity for measurement. The patent application JP-A-2-287257 which has been laid open to the public discloses a method for the measurement of G-CSF in which a surfactant as well as sodium ethylenediaminetetraacetate is contained in an antigen-antibody reaction solution as a means to eliminate an interference in body fluid components.

The reported methods for the measurement of G-CSF in body fluids are divided into (1) bioassay, (2) extraction method, and (3) immunoassay.

In (1) bioassay, the method has been reported in which a serum sample is dialyzed against an acidic buffer solution and then a sodium chloride solution, followed by cultivation of the dialysate in admixture with NFS-60 cells having the ability of G-CSF-dependent proliferation, after which the concentration of G-CSF is determined through the measurement of a $^3$H-thymidine uptake into the cells (Shirafuji et al., *Exp. Hematol.*, 17, 116–119 (1989)).

In (2) extraction method, lipids and almost proteins are removed from a plasma sample by mixing it with an organic solvent. Next, G-CSF-containing substances in the plasma sample are absorbed on an ion exchange resin in order to separate G-CSF from interfering substances by utilizing the difference in their affinities for the resin, thereby recovering G-CSF. Thereafter, to the recovered G-CSF are added a radioactively labeled G-CSF and an antibody to G-CSF, and the radioactivity of the resulting G-CSF/antibody complex is measured in order to determine the amount of G-CSF based on the measured value.

In (3) measurement of G-CSF by immunoassay, the radioimmunoassay (RIA) in which an radioisotope is used as a marker (Tanaka et al., *J. Pharmaco-bindyn*, 15, 359–366 (1992)) has been reported as well as the enzyme immunoassay (EIA) in which an enzyme is used (Motojima et al., *J. Immunol.Methods*, 118, 187–192 (1989); Ohmori et al., *Res. Exp. Med.*, 189, 163–171 (1989); *International Journal of Hematology*, vol.56, Supplement No.1, p.202; *The Japanese Journal of Clinical Hematology*, vol.33, Supplement No.10, p.1544; Tanaka et al., *J. Pharm. Exp. Ther.*, 255, 724–729 (1990); Kuwabara et al., *J. Pharmacobio-Dyn.*, 15, 121–129 (1992); JP-A-5-115297).

EIA is a method in which an antibody directed against an antigen to be measured is immobilized on a solid phase followed by reaction with the antigen, and the solid phase obtained is washed and then reacted with an enzyme-labeled antibody to determine the amount of the antigen (Ishikawa et al., *Rinsho Kagaku* (Clinical Chemistry), vol.3, p.374 (1974)).

In comparison with the above methods (1) and (2), EIA is regarded as being an accurate and simple method because it is superior in specificity and because it does not require any complex pretreatments of samples to be assayed.

Examples of the antibody to be used in EIA include polyclonal antibodies obtained from anti-sera from immunized animals, and monoclonal antibodies obtained from the supernatant of the culture of hybridomas produced by fusion of mouse spleen cells with myeloma cells. With regard to EIA of G-CSF, methods in which a polyclonal or monoclonal antibody to the G-CSF is used have been reported.

To improve the sensitivity of the EIA for G-CSF, several methods have been reported: the method in which non-specific binding is repressed by use of a digested antibody fragment as a labeled antibody; and the method in which enzymatic activity is measured by a highly sensitive fluorescence technique (*International Journal of Hematology*, vol.56, Supplement No.1, p.202) or chemiluminescence technique (*The Japanese Journal of Clinical Hematology*, vol.33, Supplement No.10, p.1544).

In studying the relationship between the G-CSF level in the body and, the etiology associated with G-CSF, it is important to accurately know normal or lower G-CSF levels in the body fluids from healthy persons or patients respectively. For example, it has been reported that the serum G-CSF level is distributed around 10 pg/ml in healthy persons, whilst it is about 3 pg/ml in patients with hematological disorders (*International Journal of Hematology*, vol.57, Supplement No.1, p.235). However, most of the assays reported can not detect a lower level of G-CSF. In only one example of EIA reported which can accurately determine a G-CSF level lower than that in healthy persons (*The Japanese Journal of Clinical Hematology*, vol.33, Supplement No.10, p.1544), polyclonal antibodies are used as first and second antibodies. This method, however, has the disadvantage that the number of measurements is limited because of the limitation of the availability of the antibodies having the same performance.

In the case of monoclonal antibody, since the quantity of the antibody obtained is theoretically infinite, the monoclonal antibody has the advantage that the number of measurements is not limited when applied to EIA. Especially, it is desirable to use a monoclonal antibody as a first antibody to be bound to an EIA solid phase because the larger amount of a monoclonal antibody is used in the EIA in comparison with the labeled antibody.

Although there is a report on an EIA using a monoclonal antibody which can detect the normal level of G-CSF in healthy persons (JP-A-5-115297), nothing is yet known about the similar method which can accurately measure both normal and lower levels.

On the other hand, the needed amount of a second antibody to be used in EIA is generally smaller than that of a first antibody to be immobilized on a solid phase. For example, while the amount of IgG which binds to a 96-well microplate is about 30 pmol/100 µl per measurement, the amount of a second antibody used in EIA of human ferritin is 5 fmol per measurement (Hasida et al., *J. Biochem.*, 108, 960–964 (1990)). Also, a polyclonal antibody having a plurality of antigen-binding sites may be useful as a labeled antibody for the construction of a highly sensitive assay system, because the number of second antibody molecules to be bound per antigen molecule captured on the solid phase becomes plural.

In addition, a problem of the insufficient sensitivity which is resulted from the interference with blood components occurs often when EIA systems are to be established. This has been reported, for example, on the cytokine EIA (Ida et al., *J. Immunol. Methods*, 156, 27–38 (1992)). In consequence, when clinical applications of G-CSF are taken into consideration, it is necessary to develop an EIA for the highly sensitive measurement of G-CSF, in which a monoclonal antibody that is not interfered with any body fluid components can be used to accurately measure normal or lower G-CSF levels in healthy persons or patients, respectively.

DETAILED DESCRIPTION OF THE INVENTION

Figure 1:
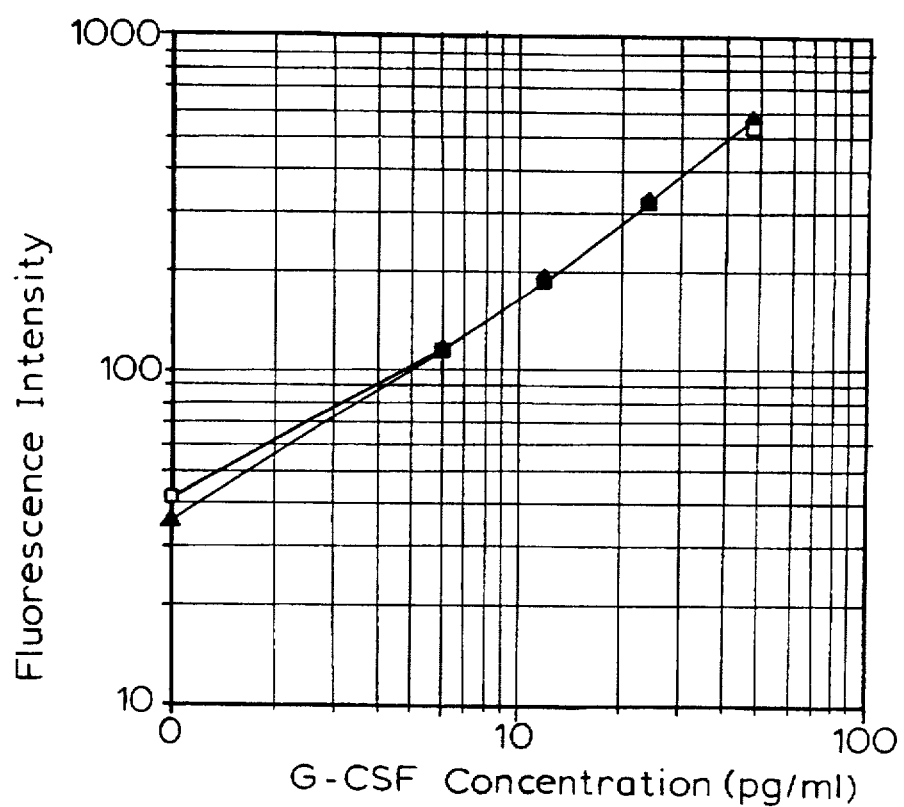
FIG. 1 shows dose-response curves regarding standard G-CSF solutions which have been diluted with the buffer solution or the standard dilution plasma in a serial dilution manner, wherein K35-2B was used as a first antibody.

To overcome the above mentioned problems, we have prepared various monoclonal antibodies to select therefrom an antibody which has a high affinity and is not interfered in the presence of body fluid components, and we have then applied the thus selected antibody to an EIA system thereby finding an excellent assay method which satisfies the above stated requirements. The present invention has been accomplished on the basis of this finding.

Accordingly, the present invention relates to an enzyme immunoassay for the measurement of human G-CSF in which the monoclonal antibody is used as an antibody to be immobilized on a solid phase.

We have fused myeloma cells with the spleen cells from mice which had been immunized with an *E. coli*-derived recombinant human G-CSF as an antigen so as to produce hybridomas of which anti-G-CSF antibody-producing cells have been then cloned. We have now succeeded in isolation of a clone capable of producing a monoclonal antibody which has high affinity for G-CSF and is not interfered with any body fluid components. [This clone, named K35-2B, has been deposited with National Institute of Bioscience and Human Technology, Agency of Industrial Science and Technology, Ministry of International Trade and Industry, under the accession number FERM BP-4340.]

In general, it is desired that an antibody used in EIA has higher affinity for G-CSF thereby increasing a sensitivity in a G-CSF EIA, because the antibody which have higher affinity in antigen-antibody reaction can form its immune complex with a more minute amount of the antigen G-CSF. The monoclonal antibody used in the present invention is a high affinity antibody which has an association constant (i.e., K value) of $1.8 \times 10^8$ l/mol.

Preferably, the labeled antibody used in the present invention is a high affinity polyclonal antibody which has a plurality of antigen recognition sites. In addition, it is preferable to use a highly specific antibody which has been purified on a G-CSF-bound affinity column.

IgG itself or its digested fragment is commonly used as an antibody to be labeled with an enzyme. Examples of the digested fragment of IgG include $F(ab')_2$ formed by pepsin digestion, Fab' obtained by further reduction of the pepsin-digested fragment, and Fab obtained by papain digestion. Enzyme-labeled products of these digested antibody fragments have the advantage that the sensitivity in measurement is increased because of their small non-specific adsorption to a solid phase used in EIA. The preferred example of the labeled antibody used in the present invention is a purified IgG, or its digested fragments, especially Fab', from the viewpoint of minimizing non-specific binding.

The enzyme used as a label in the present invention may be selected from appropriate enzymes which are conventionally used in the field of EIA where the enzyme activity is measured by means of colorimetry, enzymatic cycling colorimetry, fluorometry, bioluminescence analysis, chemiluminescence analysis, or the like. Typical examples of such enzymes include peroxidase, alkaline phosphatase and $\beta$-D-galactosidase, of which $\beta$-D-galactosidase is particularly preferred. The Fab' or labeled antibody can be prepared in accordance with the procedures commonly used in the related technical field (E. Ishikawa, "*Kohso Hyoshiki-ho* (Enzyme Labeling)", 1991, Gakkai Shuppan Center).

Examples of the body fluids to be measured in the present invention include plasma, serum, bone marrow fluid, urine, saliva, tear, sweat and the like, all of which can be collected relatively easily.

According to the present invention, G-CSF can be measured within such a range that a dose-response curve of the average reading value of enzyme activities in plural wells indicating the presence of enzyme activity vs the final concentration of G-CSF in the first reaction mixture can be prepared with high reproducibility. The detection limit of G-CSF in the present invention is defined as a G-CSF concentration readable from the dose-response curve, which corresponds to the sum of an average value of G-CSF-free samples measured (i.e., background) plus a value of 2× its standard deviation. As a result, the assay method of the present invention has a measurable range of from 0.167 to 600 pg/ml.

To further improve the sensitivity and accuracy of the assay of the present invention by eliminating any influences of interfering substances in body fluids, both a nonionic surfactant and a salt of ethylenediaminetetraacetic acid (EDTA) may preferably be added to the reaction system during the antigen-antibody reaction of human G-CSF with the insoluble antibody.

In the enzyme immunoassay of the present invention, other means and conditions that are not described herein may be those employed in the conventional EIA techniques (E. Ishikawa, "*Kohso Men-eki Sokutei-ho* (Enzyme Immunoassay)", 3rd ed., 1987, Igaku Shoin).

EXAMPLES

The following examples are provided to further illustrate the present invention. It is to be understood, however, that the spirit and scope of the present invention are not limited by those examples.

Example 1

Preparation of anti-G-CSF antibody-producing hybridoma clone

The following experiments were carried out by the method of Iwasaki et al. (T. Iwasaki et al., "*Tan Kuron Kotai* (Monoclonal Antibody)", 1983, Kodansha).

(1) Preparation of immunized mouse spleen cells

200 μg of human G-CSF per animal was emulsified in Freund's complete adjuvant (DIFCO) with mixing, and each of two 5-week-age BALB/c female mice (purchased from Charles River Japan, Inc.) was intraperitoneally immunized with the emulsified G-CSF.

Booster was carried out by repeating the intraperitoneal administration of 200 μg/animal of G-CSF emulsified in Freund's incomplete adjuvant (DIFCO) three times at intervals of two weeks. Finally, 100 μg/animal of human G-CSF diluted with physiological saline was intravenously administered into a murine tail, and the spleen cells were removed from the immunized mice 3 days after the administration, for use in cell fusion.

(2) Preparation of hybridomas

The spleen cells obtained above were suspended in RPMI 1640 medium (GIBCO) and centrifuged at 1,200 rpm for 5 minutes. After repeating the suspension/centrifugation step, the thus washed cells were mixed with mouse myeloma cells (×63, 6, 5, 3) and 1 ml of RPMI 1640 medium supplemented with 50% polyethylene glycol 4000 (Merck), and the mixture was stirred for 5 minutes to occur cell fusion. The resulting cells were suspended in RPMI 1640 medium and centrifuged at 1,200 rpm for 5 minutes, and the thus washed cells were suspended in RPMI 1640 medium containing hypoxanthine-aminopterin-thymidine (HAT) and 10% fetal calf serum (FCS) and dispensed in $5 \times 10^6$ cells/ml portions into wells of a 96-well Microplate (Pharmacia). Thereafter, the cells were cultured at 37° C. for 7 days in a 5% $CO_2$ incubator.

(3) Screening of anti-G-CSF antibody-producing clone

Human G-CSF was diluted to a concentration of 10 μg/ml with 50 mM sodium carbonate buffer (pH 9.2) containing 2% of glutaraldehyde (ex Junsei Kagaku, Japan). The resulting solution was dispensed in 100 μl portions into wells of a 96-well Amino Plate (ex Sumitomo Bakelite, Japan) and maintained overnight at 4° C. After removing the solution and washing the plate 3 times with PBS-0.05% Tween (PBS-T), PBS containing 10% skim milk was dispensed in 200 μl portions into wells of the thus washed plate, and the plate was left at room temperature for 1 to 2 hours. After removing the reaction mixture and washing the plate 3 times with PBS-T, a culture supernatant to be assayed was dispensed in 50 μl portions and incubated at room temperature for 1 hour. The plate was then washed 5 times with PBS-T, and the 1:1,000 diluted solution of an anti-mouse IgG antibody/peroxidase conjugate was dispensed in 50 μl portions and incubated at room temperature for 1 hour. After washing the plate 5 times with PBS-T, a peroxidase substrate solution (10 mmol/l of 1,2-phenylenediamine diluted with 50 mM acetate buffer (pH 5.0) containing 0.01% hydrogen peroxide) was dispensed in 50 μl portions and incubated at room temperature for 10 minutes. Thereafter, 2N sulfuric acid was dispensed in 50 μl portions into each well of the plate, and the absorbance at 492 nm was measured in order to select wells which indicated the production of a specific antibody.

(4) Cloning

Cloning of the selected specific antibody-producing hybridomas was carried out twice by limiting dilution using an aminopterin-free HT medium and a 10% FCS-containing RPMI 1640 medium, thereby obtaining the desired anti-G-CSF antibody-producing clone.

Example 2

Selection of high affinity antibody

Association constants (i.e., K values) of the monoclonal antibodies obtained in Example 1 were measured in accordance with the procedure of Sudo et al. (T. Sudo et al., "*Men-eki Jikken Sosa-ho* (Procedures for Immunological Experiments)", 1980, ed. the Japanese Immunological Society).

That is, $^{125}$I-G-CSF which has been prepared in accordance with the procedure of Kuwaki et al. (*Jpn. J. Cancer Res.*, 81, 560–563 (1990)) was diluted with PBS containing 0.1% bovine serum albumin (BSA) (BSA-PBS) and dispensed in 50 μl portions into 1.5-ml test tubes (Eppendorf). To each of the tubes were added 50 μl of a culture supernatant in which a monoclonal antibody to be measured is contained and 50 μl of G-CSF diluted to varying concentrations with 0.1% BSA-PBS, and the reaction mixture was kept for 72 hours at 4° C. After addition of an anti-mouse IgG antibody and subsequent standing at room temperature for 1 hour, the reaction mixture in each tube was centrifuged at 8,500 rpm for 5 minutes. The supernatant was discarded and the precipitated immunological reaction product was measured for its radioactivity. As a result, the antibodies having high association constants as shown in Table 1 were obtained.

TABLE 1

| Affinity of antibodies produced by the cloned hybridomas | |
|---|---|
| Lot No. | Association constant (l/mol) |
| K35-2B | $1.8 \times 10^8$ |
| K33-10D | $1.4 \times 10^8$ |
| K35-7A | $<10^8$ |
| K15-9G | $<10^8$ |

Example 3

Purification of monoclonal or polyclonal antibodies (1) Purification of monoclonal antibody The hybridoma that can produce an anti-G-CSF monoclonal antibody was suspended in the RPMI 1640 medium containing 10% FCS to a density of $3.8 \times 10^4$ cells/ml, and the suspension was cultured for 7 days. The resulting culture supernatant was concentrated about 30 times using an ultra-filtration unit (nominal molecular weight cutoff of 30,000; ex Millipore), and the IgG fraction of interest was purified on an Affi-Gel Protein A column (trade mark; ex BIO-RAD).

(2) Preparation of polyclonal antibody 0.1 mg of human G-CSF per animal was emulsified in Freund's complete adjuvant with mixing, and a sheep (Suffolk, female) was immunized with the emulsified G-CSF by its intradermal injection. Booster was carried out by repeating the intradermal injection of 0.4 to 2.0 mg/animal of human G-CSF emulsified in Freund's incomplete adjuvant four times, firstly 4 weeks after the primary immunization and then at intervals of two weeks. The whole blood was collected on the first week after the final immunization, in order to obtain an antiserum of interest.

(3) Purification of polyclonal antibody

With stirring, a saturated ammonium sulfate solution was added to the sheep anti-human G-CSF antiserum obtained as above to precipitate a crude immunoglobulin fraction at a 45% saturation level, and the precipitate was then collected by centrifugation at 2,000 rpm for 10 minutes. The precipitate was dissolved in PBS and dialyzed against the same buffer. Thereafter, the IgG fraction of interest was purified on a DEAE cellulose column (Whatman).

Example 4

Production of enzyme-labeled antibody

The following experiments were carried out in accordance with the method of Ishikawa et al. (E. Ishikawa, "*Kohso Hyoshiki-ho* (Enzyme Labeling)", 1991, Gakkai Shuppan Center).

(1) Preparation of affinity-purified Fab' from IgG 20 mg of the IgG purified by the method in Example 3 was dissolved in 0.1M acetate buffer (pH 4.5) containing 0.1M sodium chloride, and reacted with 3% by weight of pepsin at 37° C. for 36 hours. The reaction was terminated by adjusting the pH of the reaction mixture to 7.0, and unreacted IgG was removed using a protein A column (PIERCE).

Next, the resulting reaction mixture was passed through a Sepharose 4B column (trade mark; ex Pharmacia) to which G-CSF has been bound, thereby specifically binding an anti-G-CSF antibody. The antibody retained on the column was subsequently eluted with 3.2 mmol/l HCl (pH 2.5), and the eluate was adjusted to pH 7.0. After exchange of the buffer with 0.1M phosphate buffer (pH 6.0) using a Sephadex G-25 column (trade mark, ex Pharmacia), the eluate was mixed with 1/10 volume of 2-mercaptoethylamine/5 mM EDTA solution and subjected to a reduction reaction at 37° C. for 90 minutes. The reaction mixture was then subjected to gel filtration by HPLC (using TSK Gel-G3000 SW) to obtain the Fab'.

(2) Preparation of β-D-galactosidase-labeled Fab'

2.4 mg of β-D-galactosidase (Boehringer-Mannheim) was dissolved in 0.5 ml of 0.1M phosphate buffer (pH 6.0). To this was added 0.25 mg of N,N'-orthophenylene dimaleimide (Aldrich) in 5 μl of N,N'-dimethylformamide (Nakarai Chemicals Co., Japan). After reaction at 30° C. for 20 minutes, the reaction mixture was subjected to gel filtration on Sephadex G-25 to obtain β-D-galactosidase-maleimide.

Next, 160 μg of the Fab' was reacted with 230 μg of β-D-galactosidase-maleimide in 0.1M phosphate buffer (ph 6.0) containing 2.5 mM EDTA at 4° C. for 20 hours. Unreacted materials were removed by HPLC (using TSK G4000 SW-XL for gel filtration) to obtain a β-D-galactosidase-labeled Fab'.

Example 5

Production of anti-human G-CSF antibody-immobilized EIA plate

The anti-human G-CSF monoclonal antibody obtained in Example 3 (1) was diluted with PBS to a concentration of 10 μg/ml, and the solution was dispensed in 100 μl portions into each well of a 96-well EIA plate. The plate was then kept overnight for 4° C. The liquid was discarded from the plate which was then washed 3 times with PBS-T. Next, PBS containing 10% skim milk was dispensed in 300 μl portions into the wells of the plate, and the plate was kept for 1–2 hours at room temperature. After removal of the liquid, the plate was washed 3 times with PBS-T.

Example 6

Preparation of standard plasma for dilution of G-CSF

The anti-G-CSF antibody prepared in Example 3 was bound to Sepharose 4B to make an anti-G-CSF antibody-bound Sepharose 4B column. The plasma from a healthy person was diluted with an equal volume of a column diluent (2.7 mM KCl, 137 mM NaCl, 1.15 mM $K_2HPO_4$, 8 mM $Na_2HPO_4$, 1 mM phenyl methyl sulfonyl fluoride), and the plasma solution was then passed through the above column to remove the endogenous G-CSF. The thus treated plasma was mixed with a half volume of the plasma-diluting solution which is 0.3M tris(hydroxymethyl)aminomethane-HCl buffer (pH 7.3) containing 1.5% EDTA, 1.5% Tween 20, 0.3% BSA and 0.9M NaCl, thereby obtaining the desired standard plasma for use in dilution of G-CSF.

Example 7

Selection of a monoclonal antibody which is not interfered with plasma (1) EIA for human G-CSF in buffer solution A standard human G-CSF solution was diluted with equal volumes of 7% BSA-PBS, the column diluent in Example 6 and the plasma-diluting solution in Example 6, and the standard solution obtained was dispensed in 100 μl portions into wells of the EIA plate prepared in Example 5. After reaction at room temperature for 3 hours, the liquid was discarded from the plate which was then washed with the PBS-T five times. The β-D-galactosidase-labeled Fab' produced in Example 4 was diluted with an enzyme diluent (1% BSA, 0.05% $NaN_3$, 0.1M NaCl, 1 mM $MgCl_2$, 10 mM phosphate buffer, pH 7.0), and the solution was dispensed in 100 μl portions into the wells of the above plate. After reaction overnight at 4° C., the liquid was discarded and the plate was washed 5 times with PBS-T. Into the wells was dispensed 0.1 mM 4-methylumbelliferyl-β-D-galactoside in 100 μl portions. After the plate was kept at 37° C. for 6 hours, the reaction was stopped by addition of 150 μl of 2M glycine-sodium hydroxide buffer (pH 10.3) in order to measure a fluorescence intensity at an excitation of 360 nm and an emission of 450 nm.

(2) EIA for G-CSF in plasma

Human G-CSF was diluted with the standard plasma for dilution which has been prepared in Example 6, and it was measured in the same manner as in Example 7 (1).

(3) Selection of a monoclonal antibody which is not interfered with plasma

The above assays (1) and (2) were carried out in parallel in order to select an antibody showing no interference. Dose-response curves obtained under the conditions of the assays (1) and (2) using K35-2B as a first antibody are shown in FIG. 1.

Example 8

Figure 2:
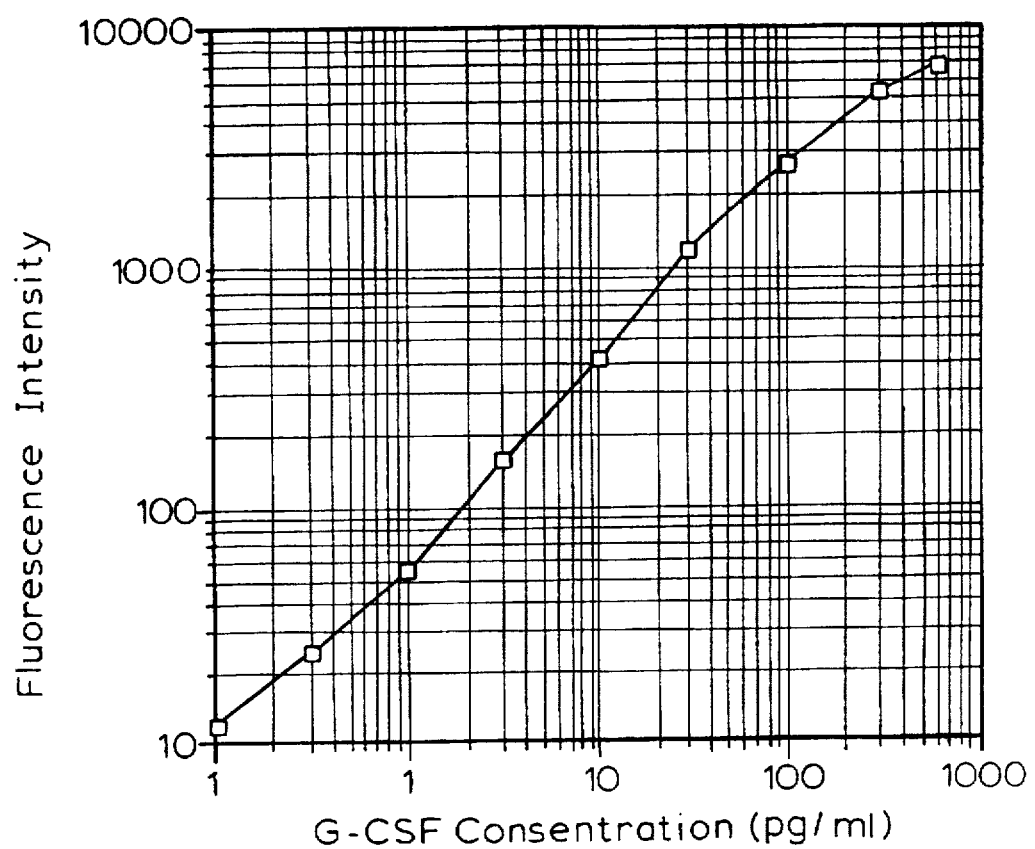
FIG. 2 shows a dose-response curve regarding the standard G-CSF solution diluted with the standard dilution plasma in a serial dilution manner.
Figure 3:
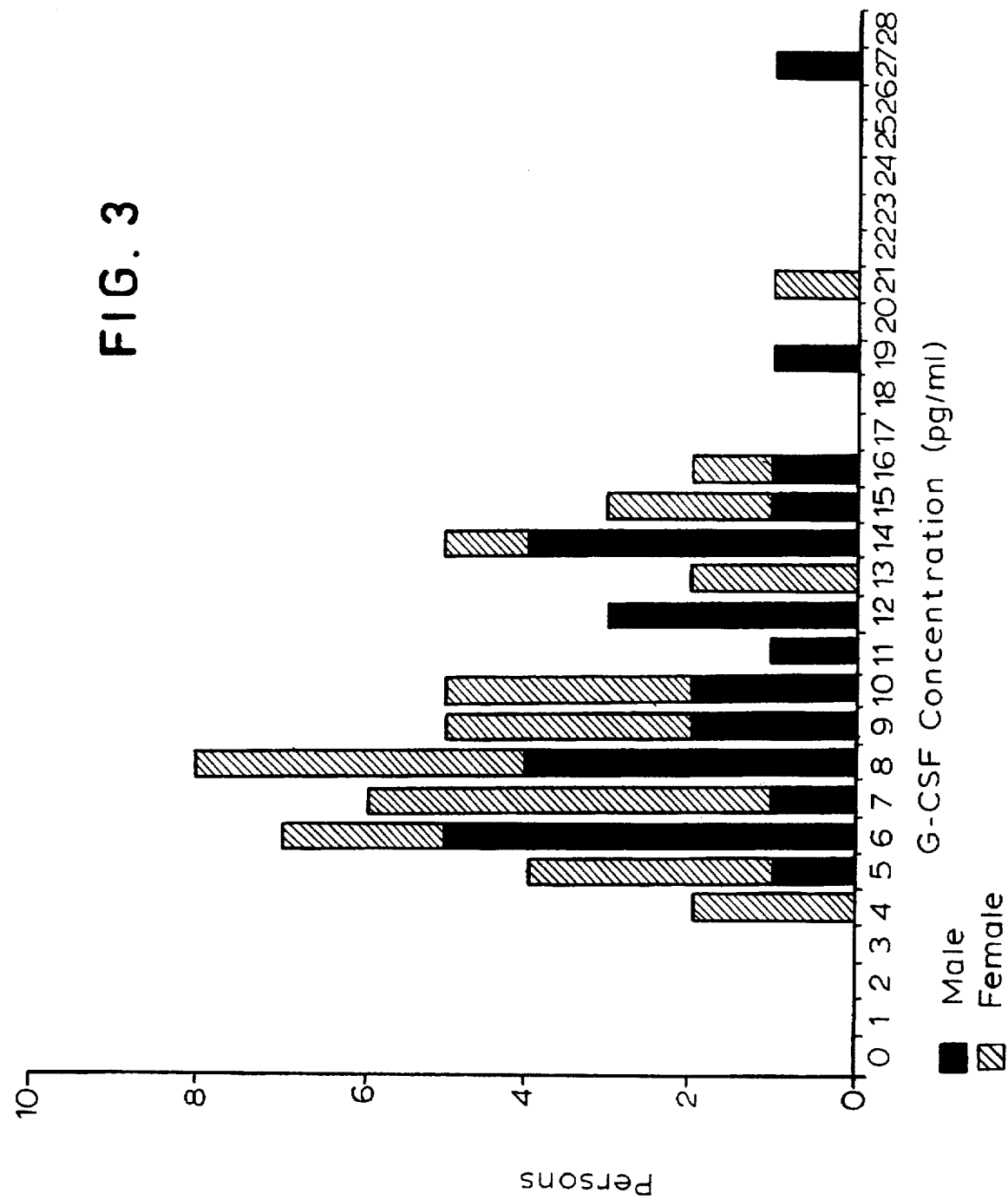
FIG. 3 shows the results of the measurement of G-CSF concentrations in plasma samples from 57 healthy volunteers (27 males of 25–45 years old and 30 females of 19–47 years old). The G-CSF concentration was 10.5 pg/ml in average.

Human G-CSF EIA using the monoclonal antibody which is not interfered with plasma (1) Measurement of plasma G-CSF An EIA plate was prepared in the same manner as in Example 5 using the monoclonal antibody produced by the K35-2B hybridoma, and the assay was carried out as described in Example 7 (2). A standard curve was made by plotting fluorescence intensities at the ordinate vs human G-CSF concentrations at the abscissa on a log-log graph paper. Since the plasma diluted in 1:3 was used in the reaction, the detection limit of G-CSF in plasma was found to be 0.5 pg/ml (see FIG. 2).

(2) Recovery test

Human G-CSF was added in an amount of 10 or 50 pg/ml to each of 10 plasma samples and assayed in accordance with the procedure described in Example 8 (1). Each sample to be assayed was prepared by adding equal volumes of the column diluent and the plasma-diluting solution, in the same manner as the standard plasma dilution method in Example 6. As a result, better recovery yields were obtained in respective concentrations. As shown in Table 2, the recovery rates of the plasma samples hardly differ from one another.

TABLE 2

| G-CSF added | 0 pg/ml | 10 pg/ml | | 50 pg/ml | |
|---|---|---|---|---|---|
| Plasma sample No. | G-CSF (pg/ml) | G-CSF (pg/ml) | Recovery (%) | G-CSF (pg/ml) | Recovery (%) |
| 1 | 14.1 | 23.7 | 96.0 | 58.1 | 88.0 |
| 2 | 13.2 | 22.9 | 97.0 | 58.4 | 90.4 |
| 3 | 14.9 | 24.5 | 96.0 | 58.4 | 87.0 |
| 4 | 8.69 | 18.4 | 97.3 | 54.9 | 92.5 |
| 5 | 10.1 | 18.6 | 85.0 | 55.2 | 90.2 |
| 6 | 8.93 | 19.3 | 103.7 | 60.0 | 102.1 |
| 7 | 15.8 | 25.0 | 92.0 | 58.5 | 85.3 |
| 8 | 13.2 | 22.3 | 91.0 | 59.3 | 92.2 |
| 9 | 23.8 | 33.0 | 92.0 | 66.2 | 84.8 |
| 10 | 20.9 | 30.1 | 92.0 | 71.0 | 100.2 |
| Average | | | 94.2 | | 91.3 |

(3) Measurement of G-CSF concentration in plasma samples from healthy volunteers Plasma samples from healthy volunteers were assayed by the method described in Example 8 (1). As shown in Table 3, the G-CSF was measurable in all of the 57 samples tested, with a sensitivity sufficient to detect not only normal G-CSF levels but also lower G-CSF levels.

TABLE 3

| | JP-A-62-130698 | JP-A-2-287257 | Ohmori et al. (1992) | Int. J. Hematol. 56 (1), 202 | JP-A-5-115297 | Present invention |
|---|---|---|---|---|---|---|
| First antibody | monoclonal antibody (MAb.) | polyclonal antibody (PAb.) | MAb. | PAb. | MAb. | MAb. |
| Second antibody | not used | PAb. | PAb. | PAb. | MAb. | PAb. |
| Fragmentation of second antibody | — | fragmented | IgG | fragmented | fragmented | fragmented |
| Detection limit | 5 ng/ml (in buffer) | ca.20 pg/ml (in buffer) | 50 pg/ml (in serum) | 9 pg/ml (in plasma) | 5 pg/ml (in serum) | 0.5 pg/ml (in plasma) |
| *1 | not described | measurable | measurable | measurable | measurable | measurable |
| *2 | impossible | impossible | impossible | partially possible | partially possible | all possible |
| *3 | impossible | impossible | impossible | impossible | impossible | possible |

*1 Measurement of G-CSF level in blood components
*2 Measurement of normal plasma G-CSF level
*3 Measurement of plasma G-CSF level lower than normal According to the present invention, the G-CSF EIA system that has now been accomplished by using the anti-human G-CSF monoclonal antibody which has high affinity for G-CSF and which is not interfered with any blood components, enables the accurate and highly sensitive measurement of the G-CSF in body fluids. For Example, the detectable level of G-CSF in plasma is 0.5 pg/ml in minimum. Thus, the G-CSF level lower than the normal G-CSF level, as well as the normal level, can be determined accurately (see Table 3). The EIA of the present invention has the advantage that the number of measurements is not limited because of the use of the monoclonal antibody which can be supplied permanently as a first antibody.

What is claimed is:

1. In a method for selecting a monoclonal anti-human Granulocyte Colony Stimulating Factor (G-CSF) antibody preparation for use in an immunoassay for quantification of human G-CSF in a human fluid sample wherein hybridoma cell lines secreting candidate monoclonal anti-human G-CSF antibodies are prepared and selected on the basis of capacity to produce monoclonal antibodies having a human G-CSF affinity of at least $1.8 \times 10^8$ l/Mol., an improvement in screening procedures for identification of candidate monoclonal antibodies capable of detecting low levels of human G-CSF in human fluid samples, said improvement comprising:

(1) preparing a series of serially diluted plasma solutions having increasing concentrations of human G-CSF using human plasma from which human G-CSF has been removed;

(2) employing a candidate monoclonal antibody as a G-CSF capture antibody in enzyme immunoassay procedures applied to plasma solutions prepared according to step (1) and preparing a standard curve of the assay result;

(3) determining a detection limit of a G-CSF concentration read from the standard curve, based on the G-CSF concentration corresponding to the sum of an average value of G-CSF-free plasma samples measured plus a value of 2 times its standard deviation; and (4) selecting candidate monoclonal anti-human G-CSF antibodies for an immunoassay of which the detection limit of G-CSF in plasma is equal or less than 0.5 pg/ml.

2. The improvement according to claim 1 wherein the enzyme immunoassay of step (2) is performed in the presence of a salt of ethylenediaminetetraacetic acid and a nonionic surfactant.

3. A monoclonal anti-human G-CSF antibody selected according to the process of claim 1.

4. A monoclonal antibody according to claim 3, a K35-2B antibody produced by the hybridoma cell line FERM Accession No.: BP4340.

5. A method for detecting human G-C SF in human plasma comprising the steps of contacting the human plasma with the monoclonal anti-human G-CSF antibody of claim 3 which is immobilized on a solid phase;

contacting the solid phase with a labeled reagent that is specific for human G-CSF; and detecting bound labeled reagent on the solid phase to detect the presence of human G-CSF in the human plasma.

* * * * *